United States Patent
McEwen et al.

(10) Patent No.: US 10,550,316 B2
(45) Date of Patent: Feb. 4, 2020

(54) METHOD OF FORMING A FRACTURING FLUID FROM PRODUCED WATER

(71) Applicant: Canadian Energy Services L.P., Calgary (CA)

(72) Inventors: John G. E. McEwen, Calgary (CA); Raquel Marie Dimmick, Weyburn (CA)

(73) Assignee: Canadian Energy Services L.P., Calgary (CA)

( * ) Notice: Subject to any disclaimer, the term of this patent is extended or adjusted under 35 U.S.C. 154(b) by 88 days.

(21) Appl. No.: 15/662,895

(22) Filed: Jul. 28, 2017

(65) Prior Publication Data
US 2018/0030335 A1 Feb. 1, 2018

Related U.S. Application Data

(60) Provisional application No. 62/368,368, filed on Jul. 29, 2016.

(51) Int. Cl.
*C09K 8/72* (2006.01)
*C07F 5/02* (2006.01)

(52) U.S. Cl.
CPC .............. *C09K 8/725* (2013.01); *C07F 5/027* (2013.01); *C08L 2205/22* (2013.01)

(58) Field of Classification Search
None
See application file for complete search history.

(56) References Cited

U.S. PATENT DOCUMENTS

| | | | |
|---|---|---|---|
| 2007/0125536 A1 | 6/2007 | Acock et al. | |
| 2008/0269082 A1 | 10/2008 | Wilson et al. | |
| 2008/0287323 A1 | 11/2008 | Li et al. | |
| 2009/0277634 A1* | 11/2009 | Case | E21B 21/062 166/275 |
| 2009/0277640 A1* | 11/2009 | Thompson | C09K 8/00 166/305.1 |
| 2009/0281006 A1* | 11/2009 | Walters | C09K 8/68 507/270 |

(Continued)

FOREIGN PATENT DOCUMENTS

| | | |
|---|---|---|
| CA | 2864203 A1 | 3/2015 |
| WO | 2015112957 A1 | 7/2015 |
| WO | 2015126395 A1 | 8/2015 |

OTHER PUBLICATIONS

Guerra et al., "Oil and Gas Produced Water Management and Beneficial Use in the Western United States" U.S. Department of the Interior Bureau of Reclamation, 2011.

(Continued)

*Primary Examiner* — John J Figueroa
(74) *Attorney, Agent, or Firm* — Borden Ladner Gervals LLP; Mark Vickers (57) ABSTRACT

The present method forms a cross linked fracturing fluid using produced water. The produced water is a brine water having a TDS content of at least 45,000 mg/L. The produced water is mixed with a crosslinkable guar. The pH of the water is adjusted for hydration, if necessary, by adding acid prior to or with the addition of the guar to the produced water. The guar is allowed to hydrate in the water. A crosslinker is added and, if necessary, a base with or after the addition of the crosslinker, wherein the base is added to adjust the pH of the water for crosslinking.

8 Claims, 4 Drawing Sheets

(56) References Cited

U.S. PATENT DOCUMENTS

| | | |
|---|---|---|
| 2010/0224365 A1 | 9/2010 | Abad |
| 2010/0248997 A1 | 9/2010 | Li et al. |
| 2010/0307757 A1 | 12/2010 | Blow et al. |
| 2011/0017677 A1* | 1/2011 | Evans .................. C02F 1/5236 210/708 |
| 2011/0082057 A1 | 4/2011 | Zhang et al. |
| 2012/0125617 A1 | 5/2012 | Gu et al. |
| 2012/0305254 A1 | 12/2012 | Chen et al. |
| 2013/0153233 A1 | 6/2013 | Bell et al. |
| 2013/0157905 A1 | 6/2013 | Saini et al. |
| 2013/0333888 A1 | 12/2013 | Rincon-Torres |
| 2014/0158354 A1 | 6/2014 | Kumar et al. |
| 2014/0174742 A1 | 6/2014 | Mirakyan et al. |
| 2014/0194327 A1* | 7/2014 | Hutchings .............. C09K 8/685 507/214 |
| 2014/0196904 A1 | 7/2014 | Fontenelle et al. |
| 2014/0374104 A1 | 12/2014 | Seth et al. |
| 2015/0013987 A1 | 1/2015 | Underwood et al. |
| 2015/0068747 A1 | 3/2015 | Hwang et al. |
| 2015/0129231 A1 | 5/2015 | Vittur et al. |

OTHER PUBLICATIONS

Stringfellow et al., "Physical, Chemical, and Biological Characteristics of Compounds Used in Hydraulic Fracturing," Journal of Hazardous Materials, Apr. 2014, vol. 275, pp. 37-54.

Sun et al., "Rheology and Convective Heat Transfer Properties of Borate Cross-linked Nitrogen Foam Fracturing Fluid," Heat Transfer Engineering, Oct. 2011, vol. 32(1), pp. 69-79.

Vengosh et al., "A Critical Review of the Risks to Water Resources from Unconventional Shale Gas Development and Hydraulic Fracturing in the United States," Environmental Science & Technology, Mar. 2017, vol. 48, pp. 8334-8348.

* cited by examiner

METHOD OF FORMING A FRACTURING FLUID FROM PRODUCED WATER

CROSS REFERENCE TO RELATED APPLICATION

This application claims priority to U.S. 62/368,368, filed Jul. 29, 2016, the entire contents of which is hereby incorporated by reference.

FIELD

The present disclosure relates generally to methods of forming fracturing fluids using produced water, and in particular using produced water having a high total dissolved solids content.

BACKGROUND

Hydraulic fracturing is a common method for stimulating the production of hydrocarbon bearing formations. Fracturing includes the steps of injecting a fluid down a wellbore at high pressure to "crack" the rock and create openings for the hydrocarbons to flow back to the well. The fracturing fluid may contain proppant such as sand or gravel to hold open the created openings in the formation. The fracturing fluid typically contains large amounts of fluid, such as water. This water is called source water and is generally potable. The fracturing fluid will also contain chemicals to aid in proppant transport, friction reduction, wettability, pH control and bacterial control. The fluid is mixed with the chemicals and proppant, and pumped down a wellbore at high pressure and into the cracks in the formation.

When using proppant, it is often necessary to include a thickener in the fluid to carry the proppant to the formation and into the cracks. Thickeners such as guar as often used since they will thin under shear during pumping but thicken at the formation when shear is no longer present. The guar may also cross link in the fluid to increase the fluid's ability to effectively carry proppant.

The standard method for producing a crosslinked hydrating guar fracturing fluid is to add a guar to source water and allow the guar to hydrate in the water; towards the end of the hydration, if necessary adjust the pH with a potassium or sodium hydroxide base; and add a crosslinker to the water. In some cases, the addition of the base and crosslinker may occur at the same time.

When producing hydrocarbons from the formation, water may also be produced including formation water, injected water from secondary recovery operations (for example waterflooding), and flowback water from completion and remedial operations. Produced water often includes other components including for example petroleum hydrocarbons, suspended and dissolved solids, acid-carbonate reaction by-products from perforation and acidizing operations, spent fracturing fluid additives, and residual production chemicals. Produced water may include water existing in formations such as aquifer water, or brackish or brine water.

Due to the large amounts of water that are required in a typical fracturing operation, it is economical and environmentally preferable to recycle produced water from a well or nearby wells and use it in fracturing fluids.

Produced water often has a high concentration of total dissolved solids (TDS), many of which are known to interfere with the stability and/or compatibility of hydraulic fracturing fluids. In particular, crosslinking guars used in hydraulic fracturing fluids typically are limited by the concentration of total dissolved solids or salts, the concentration of monovalent ions such as not but limited to sodium, potassium, bromide, bicarbonate, and chloride, and by the concentration of multivalent ions such as but not limited to calcium, magnesium, manganese, barium, strontium, iron, sulfate or carbonate. Each of these negatively influences gel hydration rates, gel cross-linking efficiency, shear stability, and gel thermal stability. As a result, the base fluid used in cross-linked hydraulic fracturing fluids has been limited and potable water is commonly used.

Potable water would typically contain less than 3000 mg/L of TDS. Brackish water would typically contain about 3,000-10,000 mg/L of TDS. Saline water would contain over 10,000 mg/L of TDS while brines having a salinity greater than seawater typically have about 35,000 mg/L. Water suitable for use in fracturing fluids generally contain less than about 42,000 mg/L of TDS (although lower amounts are preferred) to limit the interference of these components with the formation and operation of the fracturing fluid. Some problems in forming fracturing fluids from water having high concentrations of TDS may include interference with the hydration of the polymer, formation of scale, interference with the breakers, polymer oxidation, unwanted delay of crosslinking, and crosslinker precipitation.

| Water Property | Typical targets for use in hydraulic fracturing fluids |
|---|---|
| pH | 6-8.5 |
| Calcium and Magnesium | <2000 ppm |
| Iron | <10 ppm |
| Barium and Strontium | <5 ppm |
| Chlorides | <40,000 ppm |
| Bicarbonates | <300 ppm |
| Phosphates | <5 ppm |
| Sulphates | <500 ppm |

Boron present in produced water may be problematic in recycling the produced water for fracturing applications. In some crosslinking guar systems, boron is used in the crosslinking process. The boron in solution in the produced water may participate in crosslinking the polymer solution formed in the produced water and compete with the boron purposefully added as the crosslinker. The additional boron in the produced fluid may cause the fluid to crosslink prematurely, and/or overcrosslink. Boron levels in produced fluid may be 10 mg/L or higher but typically operators look for water with boron levels less than this level for use in hydraulic fracturing fluids since this is generally considered to be low enough not to interfere with the crosslinking process.

It is therefore desirable to be able to avoid the use of potable water in fracturing fluids and instead use produced water from formations in fracturing formations without negatively affecting the fracturing fluid formation or operation including the cross-linking gel hydration in the fluid. The use of produced water would provide economic as well as environmental benefits to operators.

SUMMARY

It is an object of the present disclosure to obviate or mitigate at least one disadvantage of previous systems.

The present disclosure provides a method of forming a crosslinked fracturing fluid using produced water. The produced water has a high total dissolved solids content. In one aspect, the polymer, crosslinker, acid and base are added to the produced fluid in an established order to successfully hydrate and crosslink the fluid.

In one aspect, the method comprises mixing a produced brine water having a high TDS content with a polymer, adjusting the pH of the water for hydration by adding acid prior to or with the addition of the polymer to the produced water and allowing the polymer to hydrate. In a further aspect, the polymer is a crosslinkable polymer and the method would include the additional steps of adding a crosslinker to the polymer and, if necessary, adding a base with or after the addition of the crosslinker, wherein the base is added to adjust the pH of the water for crosslinking, to form a crosslinked fracturing fluid In another aspect, the method comprises the steps of: i) mixing a produced brine water having a TDS content of at least 45,000 mg/L with a crosslinkable guar; ii) adjusting the pH of the water for hydration, if necessary, by adding acid prior to or with the addition of the guar to the produced water; iii) allowing the guar to hydrate in the water; iv) adding a crosslinker and, if necessary, adding a base with or after the addition of the crosslinker, wherein the base is added to adjust the pH of the water for crosslinking, to form a crosslinked fracturing fluid. In a further aspect, the crosslinker is a borate crosslinker.

In one aspect, the produced water has a high boron content. In another aspect, the produced water is produced water from the Bakken formation. In another aspect, the method does not include a water softening step.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a method for forming a fracturing fluid using produced water. The produced water used herein has a high total dissolved solids (TDS) content. Although some produced waters may have a lower content of these contaminants, the disclosure herein applies to produced waters having these higher contents, such as water produced from the Bakken formation.

A high total dissolved solids (TDS) content is one that is above 45,000 mg/L, in another aspect above 100,000 mg/L, and in a further aspect above 150,000 mg/L. TDS is often synonymous with total salt concentration and therefore the produced water used in the present method is also considered to have a high salt concentration. One example of produced water useful in the present method is water produced from the Bakken formation.

It is expected that produced waters having a high TDS content may also have a high boron content. A high boron content may be above 20 mg/L, in another aspect it may be above 50 mg/L, in another aspect it may be above 100 mg/L, and in a further aspect, above 150 mg/L.

Waters produced from the Bakken formation are an order of magnitude higher in TDS and dissolved salts content than other produced waters. Bakken brine compositions are prone to forming a precipitate when the pH is increased, limiting the choice of bases. Bakken produced waters are high in hardness. However, the method set out herein for forming the fracturing fluid using these produced waters does not require any water treatment or water softening.

It has been found that when using produced waters for forming fracturing fluids, the steps of addition of the component are critical to successfully forming the fluid. In fracturing fluids using a crosslinking polymer, the crosslinking polymer is allowed to hydrate in the fluid before addition of the crosslinking agent.

The polymer hydration step generally occurs at a pH below 7. In one aspect, it occurs in the range of 3-7 and in a further aspect, it occurs in the range of 5-7. During the polymer hydration step, it is necessary to add acid either prior to or during the hydration stage if boron is present in the produced water. The amount of acid will vary depending on the particular fluid system and amount of boron present in the fluid but generally, a little acid needs to be added to attain optimal hydration of the guar in the produced water.

Once hydration has occurred, the crosslinker is added to the fluid. Crosslinking occurs in an alkaline pH environment, generally in a pH greater than 8 and preferably in the range of 9-11. To achieve this pH, a base is often added to the fluid. In previous methods of forming fracturing fluids, the order of addition of the crosslinker and base is not critical. In some cases, the addition of the crosslinker would be sufficient to adjust the pH without the need for additional base. In other cases, the base could be added before, at the same time as, or after addition of the crosslinker. However, with produced fluids, it is now known that to obtain optimal crosslinking, the order of addition is critical. The crosslinker must be added prior to or simultaneously with the pH adjustment to the target crosslink pH. Adjusting the pH first results in the precipitation of salts and a weak gel exhibiting significant syneresis. It is thought that because of the initial addition of acid in the hydration step, the addition of the crosslinker is not sufficient to shift the pH high enough for crosslinking to occur. If the base is added first followed by the crosslinker, the resultant crosslink is poor. If the crosslinker is added first, followed by the base for pH adjustment, or if they are added at the same time, then a good crosslink may be obtained.

It is believed that the order of addition in the crosslinking step is likely important for multiple reasons. One reason is that if the pH is adjusted towards the alkaline ahead of the crosslinker, the boron already present in the produced water will partially crosslink and negatively affect the effect of adding the borate crosslinker. Another reason is that an alkaline pH shift of produced water can induce scale to form (or precipitate) and this might potentially negatively impact the crosslinking chemistry.

Produced waters from different formations will have varying levels of contaminants and as a result, their use in fracturing fluids will vary. However, it has been found that produced waters having high TDS content, as set out above, can be successfully used to form fracturing fluids if the addition of the components in the system follows the particular order disclosed herein.

A number of hydratable crosslinkable polymers are commonly used in fracturing fluids. These include for example, guar, hydroxyethyl guar (HEG), hydroxypropyl guar (HPG), carboxyalkyl guar (CMG), and mixtures thereof. References to guar herein include guar or any of its derivatives. Similarly, any suitable cross linkers may be used including borate crosslinkers and zirconium crosslinkers.

Any suitable acid or bases may be added to adjust the pH of the fluids. Examples of acids include formic acid, acetic acid, citric acid, hydrochloric acid, and sulfamic acid. Examples of bases include potassium hydroxide, sodium hydroxide, potassium carbonate, monoethanolamine, methoxypropylamine, and a borate based crosslinker formulated with additional potassium hydroxide.

Bakken Produced Water

We tried prior methods of mixing to form a fracturing fluid with Bakken produced water but were not successful. The method outlined in Trican patent publication US2014/0194327 of using only a weak base did not work for Bakken produced water. However, the procedure set out herein for Bakken produced water was successful. It combines a low pH for guar hydration with the correct addition sequence of borate crosslinker and base which allows this method to overcome at once any boron present, the high TDS, and enhanced scaling tendency of the Bakken produced water at higher pH in order to form a fracturing fluid.

Bakken produced water in South East Saskatchewan contains a high level of dissolved salts (high TDS). Bakken water has a high TDS and high TDS waters have in the past been typically avoided for use in fracturing due to the problems in forming the fracturing fluid.

A water analysis for typical Bakken produced water is set out below in Table 1. Boron content was approximately 130 ppm. Total TDS is calculated to be 156,426 mg/L. A water analysis of a typical source water (Kisbey Source Water) in contrast, has a TDS of 858 mg/L.

TABLE 1

Comparison of Ion Content in Potable and Produced Waters

| Ion | Patent CA 2864203 Formation Water, ppm | PureChem Bakken Produced Water, ppm | Kisby Source Water (mg/L) |
|---|---|---|---|
| Calcium | 149 | 2309.5 | 65.2 |
| Magnesium | 102 | 549.1 | 45.4 |
| Barium | 180 | 0.16 | 0.1 |
| Strontium | 26 | 74.8 | 0.43 |
| Iron | 73.2 | 26.49 | 0.06 |
| Aluminum | 0.0777 | (not measured) | (not measured) |
| Boron | 126 | 130 | (not measured) |
| Manganese | 1.09 | 0.82 | 0.26 |
| Chloride | 10400 | 91868 | 150 |
| Bicarbonate | 330* | 366 | 365 |
| Sulfate | 10.9 | 2282 | 105 |
| Total Dissolved Solids (TDS) | 18900 | 156426 | 857.8 |
| pH | 6.99 | 6.93 | 7.95 |

*(calc from Alkalinity calc as CaCO3 at 542)
*boron and aluminum in Kisby source water (potable water) is expected to be minimal We initially attempted the traditional industry approach to form a fracturing fluid with the Bakken produced water. This involves hydrating the guar for 5 minutes using a Waring blender at the desired loading to form the linear gel followed by adding a borate-based crosslinker to form the crosslinked gel. The water we typically use for lab work is a so called "source water" with a pH of approximately 7-8 depending on the sample. In some cases, the pH would be adjusted to be more alkaline using sodium hydroxide towards the end of the hydration period and immediately prior to the borate addition. The sodium hydroxide buffer is added ahead of the borate crosslinker because crosslinking occurs within seconds and liquids added afterwards will not diffuse though the crosslinked fluid. The reason for adding the base is that a higher pH can yield a stronger, more stable crosslink.

The initial pH of our Bakken water samples was typically just below 7. Hydrating the guar in the produced water as provided and then adding a borate crosslinker resulted in a crosslinked fluid characterized by significant syneresis and lacking the cohesiveness required to allow for a typical 'lip test'. In some previous work with a produced water having a TDS (about 7900 ppm) lower than Bakken produced water, we were able to obtain a good crosslinked gel when the pH was adjusted to between 7-8 prior to hydrating and crosslinking so we tried the same. When we attempted to add potassium hydroxide after hydration and prior to the borate crosslinker, the fluid gave the appearance of being partially crosslinked. Adding the base and crosslinker at the same time (either as two products or pre-blended together) did not help. The resulting gel was weak and exhibited significant syneresis.

TABLE 2

Overview of preliminary work using traditional mixing sequences

| | |
|---|---|
| Fast Hydrating Guar (FHG) content in Slurry | 47% w/w |
| Slurry loading | 5-6 L/m3 |
| pH | Approx 7 |
| Typical linear visc | Varied 1-22.5 |
| Linear Fluid appearance | Watery to semi-cross linked/lumpy |
| Crosslink appearance | No crosslink to weak gel with extensive syneresis |

We also probed whether scale formation might be contributing to the problem so we attempted the use of chelators (EDTA) and scale inhibitors (phosphonate-based) without success.

Generating a Stable Crosslink:

We lowered the pH of the Bakken water to approximately 4, hydrated the guar and then added simultaneously the crosslinker and base (in this case KOH). For the first test we estimated the amount of base we would need to hit the target pH. This resulted in a stable gel with minimal syneresis.

Developing the Crosslink Procedure:

It became apparent that three components were important to obtain a suitable, stable crosslink:

1. Acidification of the Bakken water at some point in the guar hydration step.
2. Adjustment of the pH back to alkaline conditions to allow for borate crosslinking to occur.
3. Boron crosslinker added either ahead of or at the same time as pH adjustment.

| Method | Hydration Step (Total hydration time 5 min) | Crosslink Step |
|---|---|---|
| I | Acid added 1 min into slurry hydration | Crosslinker added first followed immediately by base |
| II | Acid added 1 min into slurry hydration | Crosslinker and base added at the same time |
| III | Acid added to water before slurry | Crosslinker added first followed immediately by base |
| IV | Acid added to water before slurry | Crosslinker and base added at the same time |

A linear fluid viscosity study was completed to determine the amount of acid required to obtain maximum hydration or viscosity. The study was completed by attempting to hydrate 47% FHG Slurry added at 4.5 L/m3 and varying the loadings of 23.3% Formic Acid. We found that the viscosity of the linear fluid did not change significantly from low to high additions of acid; however, hydration was incomplete in its absence. The Hydration Step of Method I was used for the study.

TABLE 3

Linear Viscosity of a 47% FHG Slurry at 4.5 L/m3 in Bakken produced water as a function of acid addition.

| Amount of 23.3% Formic Acid (L/m3) | Linear Fluid pH | Linear Fluid Viscosity (cP) |
|---|---|---|
| 0 | 6.93 | 9.5 |
| 0.5 | 5.91 | 14 |
| 1 | 5.04 | 14.5 |
| 1.5 | 4.43 | 14.5 |
| 2.0 | 4.06 | 15 |
| 2.5 | 3.79 | 14.5 |
| 3.0 | 3.57 | 14.5 |
| 3.5 | 3.45 | 14.5 |
| 4.0 | 3.34 | 14.5 |
| 4.5 | 3.24 | 14.5 |

Figure 1:
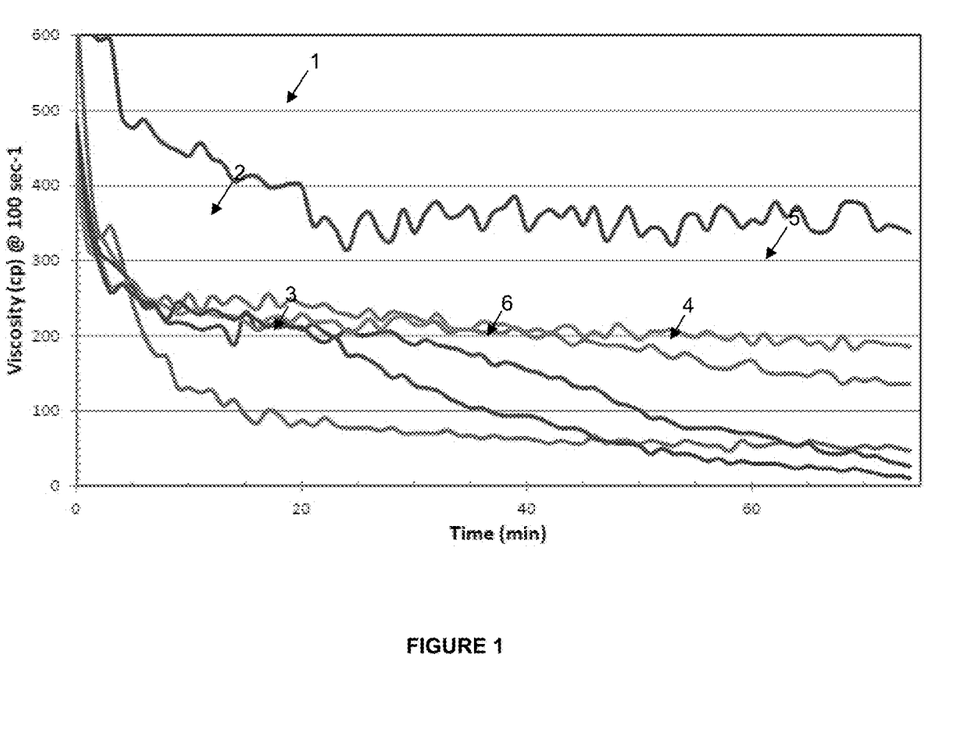
FIGS. 1-3 are stability charts for crosslinked fluids prepared according to the method disclosed herein.
Figure 2:
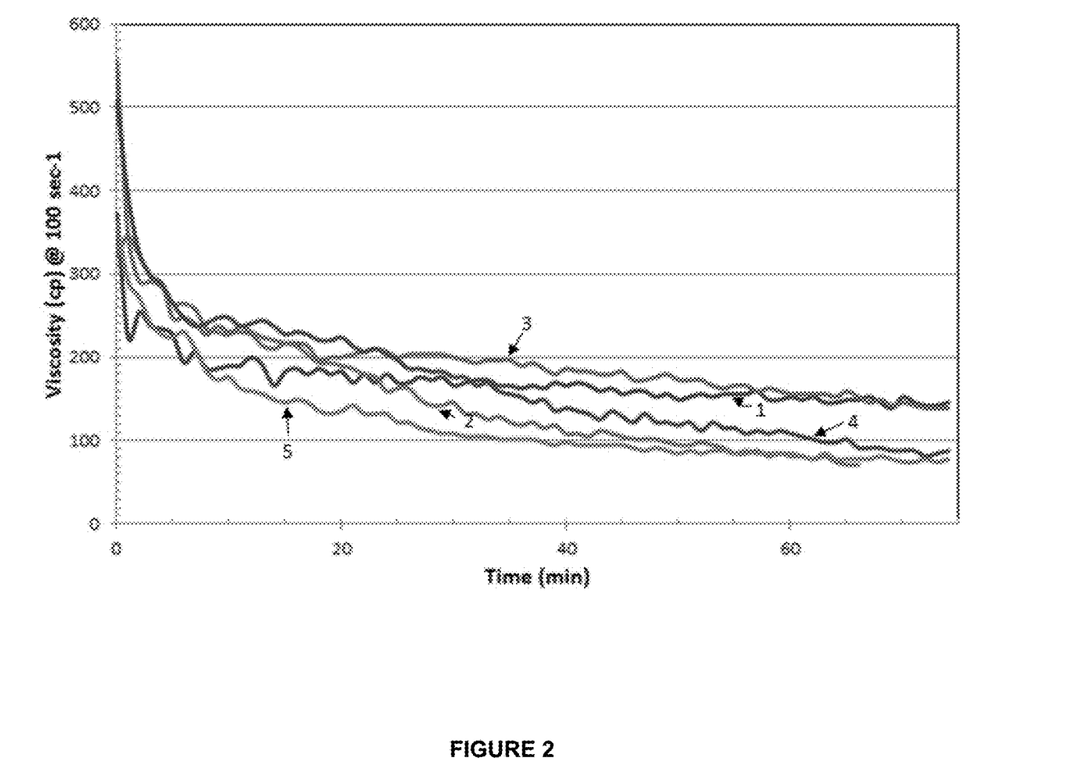
Figure 3:
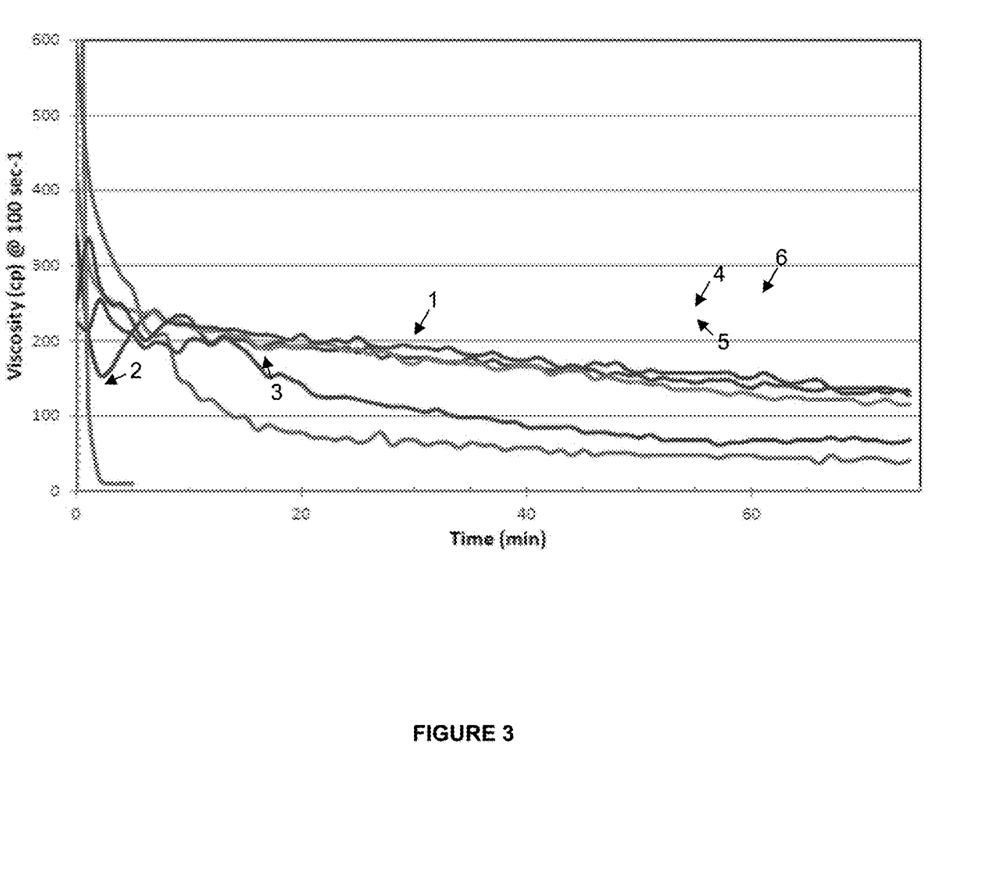

Investigating the Effect of Various Acids and Bases with the Different Crosslinking Methods on Gel Stability A variety of acids and bases were evaluated to determine how much the choice of chemicals might impact the performance of the system. The acids evaluated included formic acid, acetic acid, citric acid, hydrochloric acid, and sulfamic acid. The bases evaluated included potassium hydroxide, sodium hydroxide, potassium carbonate, monoethanolamine, methoxypropylamine, and a borate based crosslinker formulated with additional potassium hydroxide. The latter would be an example of following Method I since the crosslinker and base addition are formulated together. The experiments are summarized in Table 4. The crosslinked fluids were run on a Brookfield PVS rheometer at 70° C. The results are shown in FIGS. 1-3. These are stability charts. The overall results were acceptable.

TABLE 4

Investigation of various crosslinking methods using different acids and bases

| Test Number | Chart Number | 47% Guar Slurry Loading (L/m³) | Method | Acid | Acid Loading (L/m³) | Linear Fluid pH | Base | Base Loading (L/m³) | Crosslink pH | Stability Result |
|---|---|---|---|---|---|---|---|---|---|---|
| 150819-5P1 | C1 | 6 | II | 17% Formic Acid with choline chloride | 2.85 | 3.93 | 14% KOH | 12 | 9.64 | Stable |
| 150819-7P1 | C1 | 4.5 | II | 17% Formic Acid with choline chloride | 2.9 | 3.93 | 14% KOH | 12 | 8.69 | Stable |
| 150824-3P1 | C1 | 4.5 | II | 23.3% Formic Acid | 2.2 | 3.95 | 10% NaOH | 12 | 8.70 | Stable |
| 150824-4P2 | C1 | 4.5 | II | 23.3% Formic Acid | 2.2 | 3.95 | 45% KOH | 3.75 | 9.12 | Stable |
| 150825-1P1 | C1 | 4.5 | II | 23.3% Formic Acid | 2.25 | 3.94 | 50% NaOH | 2.4 | 8.62 | Stable |
| 150825-2P2 | C1 | 4.5 | II | 23.3% Formic Acid | 2.25 | 3.94 | 14% KOH | 12 | 8.69 | Stable |
| 151022-1P1 | C2 | 4.5 | II | 10% HCl | 1.8 | 5.07 | 14% KOH | 12 | 8.90 | Stable |
| 151022-2P1 | C2 | 4.5 | II | 20% Acetic Acid | 1.85 | 5.03 | 14% KOH | 12 | 8.55 | Stable |
| 151022-3P1 | C2 | 4.5 | II | 20% Citric Acid | 1.85 | 5.03 | 14% KOH | 12 | 8.36 | Stable |
| 151023-1P1 | C2 | 4.5 | II | 10% Sulfamic Acid | 5.45 | 5.07 | 14% KOH | 12 | 8.97 | Stable |
| 151023-2P1 | C2 | 4.5 | II | 23.3% Formic Acid | 1.05 | 5.06 | 100% Monoethanolamine | 12 | 10.09 | Stable |
| 151103-1P1 | C3 | 4.5 | II | 23.3% Formic Acid | 1.1 | 4.96 | 100% Methoxypropylamine | 12 | 9.91 | Stable |
| 151103-2P2 | C3 | 4.5 | II | 23.3% Formic Acid | 1.1 | 4.96 | 20% Potassium Carbonate | 12 | 8.16 | Not Stable |
| 151103-3P1 | C3 | 4.5 | I | 23.3% Formic Acid | 1.05 | 5.10 | Blend of 10.3% Boric Acid and 16.6% KOH | 6 | 8.36 | Stable |
| 151103-4P2 | C3 | 4.5 | II | 23.3% Formic Acid | 1.05 | 5.10 | 25% KOH | 6 | 8.07 | Stable |
| 151104-1P1 | C3 | 4.5 | III | 23.3% Formic Acid | 1 | 5.35 | 14% KOH | 12 | 8.96 | Stable |
| 151104-2P2 | C3 | 4.5 | III | 23.3% Formic Acid | 1 | 5.35 | 25% KOH | 6 | 7.68 | Stable |

The testing for FIG. 1 is set out below:

TABLE C1

Data for FIG. 1 Stability Chart

| Additives | Units | TEST1 Amount | TEST2 Amount | TEST3 Amount | TEST4 Amount | TEST5 Amount | TEST6 Amount |
|---|---|---|---|---|---|---|---|
| 47% Guar Slurry | l/m3 | 6.00 | 4.50 | 4.50 | 4.50 | 4.50 | 4.50 |
| 17% Formic Acid with Choline Chloride | l/m3 | 2.85 | 2.90 | — | — | — | — |
| 23.3% Formic Acid | l/m3 | — | — | 2.90 | — | — | — |
| 10% NaOH | l/m3 | — | — | 12.00 | — | — | — |
| 45% KOH | l/m3 | — | — | — | 3.75 | — | — |
| 50% NaOH | l/m3 | — | — | — | — | 2.40 | — |
| 14% KOH | l/m3 | 12.00 | 12.00 | — | — | — | 12.00 |
| 12% Boric Acid Crosslinker | l/m3 | 1.00 | 0.80 | 0.80 | 0.80 | 0.80 | 0.80 |

TABLE C1-continued

Data for FIG. 1 Stability Chart

| Additives | Units | TEST1 Amount | TEST2 Amount | TEST3 Amount | TEST4 Amount | TEST5 Amount | TEST6 Amount |
|---|---|---|---|---|---|---|---|
| | | Fluid Properties | | | | | |
| Fluid System | | ELE-Stim | ELE-Stim | ELE-Stim | ELE-Stim | ELE-Stim | ELE-Stim |
| Source Water | | BakkenPW | BakkenPW | BakkenPW | BakkenPW | BakkenPW | BakkenPW |
| Test Name | | 150819-5P1 | 150819-7P1 | 150824-3P1 | 150824-4P2 | 150825-1P1 | 150825-2P2 |
| Test Date | M/D/Y | Aug. 19, 2015 | Aug. 19, 2015 | Aug. 24, 2015 | Aug. 24, 2015 | Aug. 25, 2015 | Aug. 25, 2015 |
| Initial pH | pH | 6.74 | 6.74 | 6.83 | 6.83 | 6.84 | 6.84 |
| Linear pH | pH | 3.93 | 5.33 | 8.95 | 3.95 | 3.94 | 3.94 |
| Linear Viscosity | cP | 22.0 | 14.5 | 15.0 | 15.0 | 13.0 | 13.0 |
| Crosslinked pH | pH | 9.64 | 8.69 | 8.70 | 9.12 | 8.62 | 8.69 |
| Test Temperature | ° C. | 70.1 | 70.0 | 69.9 | 70.0 | 70.0 | 70.0 |
| | | Break Profile | | | | | |
| Initial Viscosity | cP | 767 | 474 | 636 | 480 | 414 | 484 |
| 15 min Viscosity | cP | 413 | 246 | 94 | 232 | 219 | 228 |
| 30 min Viscosity | cP | 338 | 225 | 71 | 188 | 215 | 134 |
| 60 min Viscosity | cP | 355 | 167 | 54 | 71 | 188 | 30 |
| Break Time (10 cP) | hh:mm:ss | N/A | N/A | N/A | N/A | N/A | N/A |

The testing for FIG. 2 is set out below:

TABLE C2

Data for FIG. 2 Stability Chart

| Additives | Units | TEST1 Amount | TEST2 Amount | TEST3 Amount | TEST4 Amount | TEST5 Amount |
|---|---|---|---|---|---|---|
| 47% Guar Slurry | l/m3 | 4.50 | 4.50 | 4.50 | 4.50 | 4.50 |
| 10% HCl | l/m3 | 1.80 | — | — | — | — |
| 20% Acetic Acid | l/m3 | — | 1.85 | — | — | — |
| 20% Citric Acid | l/m3 | — | — | 1.85 | — | — |
| 10% Sulfamic Acid | l/m3 | — | — | — | 5.45 | — |
| 23.3% Formic Acid | l/m3 | — | — | — | — | 1.05 |
| 14% KOH | l/m3 | 12.00 | 12.00 | 12.00 | 12.00 | — |
| 100% Monoethanolamine | l/m3 | — | — | — | — | 12.00 |
| 12% Boric Acid Crosslinker | l/m3 | 0.80 | 0.80 | 0.80 | 0.80 | 0.80 |
| | | Fluid Properties | | | | |
| Fluid System | | ELE-Stim | ELE-Stim | ELE-Stim | ELE-Stim | ELE-Stim |
| Source Water | | BakkenPW | BakkenPW | BakkenPW | BakkenPW | BakkenPW |
| Test Name | | 151022-1P1 | 151022-2P1 | 151022-3P1 | 151023-1P1 | 151023-2P1 |
| Test Date | M/D/Y | Oct. 22, 2015 | Oct. 22, 2015 | Oct. 22, 2015 | Oct. 23, 2015 | Oct. 23, 2015 |
| Initial pH | pH | 6.60 | 6.63 | 6.64 | 6.66 | 6.68 |
| Linear pH | pH | 5.07 | 5.03 | 5.03 | 5.07 | 5.06 |
| Linear Viscosity | cP | 14.0 | 14.0 | 14.0 | 14.0 | 14.0 |
| Crosslinked pH | pH | 8.90 | 8.55 | 8.36 | 8.97 | 10.09 |
| Test Temperature | ° C. | 70.0 | 70.0 | 70.0 | 70.1 | 70.0 |
| | | Break Profile | | | | |
| Initial Viscosity | cP | 373 | 556 | 322 | 508 | 363 |
| 15 min Viscosity | cP | 183 | 217 | 217 | 227 | 146 |
| 30 min Viscosity | cP | 166 | 146 | 200 | 176 | 108 |
| 60 min Viscosity | cP | 152 | 81 | 156 | 108 | 85 |
| Break Time (10 cP) | hh:mm:ss | N/A | N/A | N/A | N/A | N/A |

The testing for FIG. 3 is set out below:

TABLE C3

Data for FIG. 3 Stability Chart

| Additives | Units | TEST1 Amount | TEST2 Amount | TEST3 Amount | TEST4 Amount | TEST5 Amount | TEST6 Amount |
|---|---|---|---|---|---|---|---|
| 47% Guar Slurry | l/m3 | 4.50 | 4.50 | 4.50 | 4.50 | 4.50 | 4.50 |
| 23.3% Formic Acid | l/m3 | 1.10 | 1.10 | 1.05 | 1.05 | 1.00 | 1.00 |
| 100% Methoxypropylamine | l/m3 | 12.00 | — | — | — | — | — |
| 20% Potassium Carbonate | l/m3 | — | 12.00 | — | — | — | — |

TABLE C3-continued

Data for FIG. 3 Stability Chart

| Additives | Units | TEST1 Amount | TEST2 Amount | TEST3 Amount | TEST4 Amount | TEST5 Amount | TEST6 Amount |
|---|---|---|---|---|---|---|---|
| 10.3% Boric Acid and 16.6% KOH | l/m3 | — | — | 6.00 | — | — | — |
| 25% KOH | l/m3 | — | — | — | 6.00 | — | 6.00 |
| 14% KOH | l/m3 | — | — | — | — | 12.00 | — |
| 12% Boric Acid Crosslinker | l/m3 | 0.80 | 0.80 | — | 0.80 | 0.80 | 0.80 |
| Fluid Properties | | | | | | | |
| Fluid System | | ELE-Stim | ELE-Stim | ELE-Stim | ELE-Stim | ELE-Stim | ELE-Stim |
| Source Water | | BakkenPW | BakkenPW | BakkenPW | BakkenPW | BakkenPW | BakkenPW |
| Test Name | | 151103-1P1 | 151103-2P2 | 151103-3P1 | 151103-4P2 | 151104-1P1 | 151104-2P2 |
| Test Date | M/D/Y | Nov. 3, 2015 | Nov. 3, 2015 | Nov. 3, 2015 | Nov. 3, 2015 | Nov. 4, 2015 | Nov. 4, 2015 |
| Initial pH | pH | 6.69 | 6.69 | 6.65 | 6.65 | 6.72 | 6.72 |
| Linear pH | pH | 4.96 | 4.96 | 5.10 | 5.10 | 5.35 | 5.35 |
| Linear Viscosity | cP | 14.0 | 14.0 | 13.5 | 13.5 | 13.5 | 13.5 |
| Crosslinked pH | pH | 9.91 | 8.16 | 8.36 | 8.07 | 8.96 | 7.68 |
| Test Temperature | ° C. | 70.0 | 70.0 | 70.0 | 70.0 | 70.0 | 70.0 |
| Break Profile | | | | | | | |
| Initial Viscosity | cP | 339 | 12.79 | 583 | 225 | 413 | 252 |
| 15 min Viscosity | cP | 185 | | 98 | 201 | 207 | 212 |
| 30 min Viscosity | cP | 108 | | 68 | 178 | 169 | 191 |
| 60 min Viscosity | cP | 68 | | 47 | 138 | 129 | 151 |
| Break Time (10 cP) | hh:mm:ss | N/A | 0:03:06 | N/A | N/A | N/A | N/A |

From the testing and results set out above and in FIGS. 1-3, it is apparent that apart from one exception, the choice of acid or base chemistry seems to be unimportant. The exception was the potassium carbonate. It is thought that this negative result was possibly due to the enhanced scale formation that occurs when both the pH and total carbonate of the system are increased. It was observed that a white material formed as the fluids crosslinked. In most cases it appeared as flakes or 'chunks' throughout the fluid. For the potassium carbonate addition, the white material that appeared was more evenly distributed and could be described as 'white wisps' throughout the fluid. Based on previous experience, the white material was thought to be scale forming as the pH of the fluid was rapidly increased and trapped in the gel matrix with the concurrent crosslinking reaction.

Investigation of Adding Breakers to Guar Crosslinked in Bakken Produced Water

Generally, fracturing fluids are formulated not only to crosslink, but also for the fluid to break down after injection into the formation. In our testing, a gel is considered broken once three consecutive viscosity readings on the Brookfield PVS Rheometer are less than 10 cP; readings are acquired every minute. Break tests were completed using encapsulated ammonium persulfate breakers (EAPB) to break the crosslinked gel at 70° C. (with the instrument under 800 psi). Method I was used to build the crosslinked fluid and both low and high temperature EAPBs were evaluated. For our conditions, the low temperature EAPB at a loading of 0.3 kg/m3 gave a satisfactory break time. The results are shown in Table 5 and FIG. 4.

TABLE 5

Investigation in using breakers with crosslinked fluid made with Bakken produced water

| Test Number | Chart Number | 47% Guar Slurry Loading (L/m³) | Method | Acid | Acid Loading (L/m³) | Linear Fluid pH | Breaker | Breaker Loading (kg/m³) | Base | Base Loading (L/m³) | Crosslink pH | Break Time (h:mm:ss) |
|---|---|---|---|---|---|---|---|---|---|---|---|---|
| 150820-1P1 | C4 | 4.5 | II | 10.2% Formic Acid | 5.3 | 3.94 | High Temp. | 0.2 | 14% KOH | 12 | 8.80 | 2:38:05 |
| 150820-3P1 | C4 | 4.5 | II | 10.2% Formic Acid | 5.3 | 3.94 | High Temp. | 0.3 | 14% KOH | 12 | 8.63 | 2:27:05 |
| 150821-1P1 | C4 | 4.5 | II | 23.3% Formic Acid | 2.3 | 3.93 | High Temp. | 0.4 | 14% KOH | 12 | 8.86 | 2:18:05 |
| 150821-2P2 | C4 | 4.5 | II | 23.3% Formic Acid | 2.3 | 3.93 | Low Temp. | 0.3 | 14% KOH | 12 | 8.84 | 0:48:05 |

Figure 4:
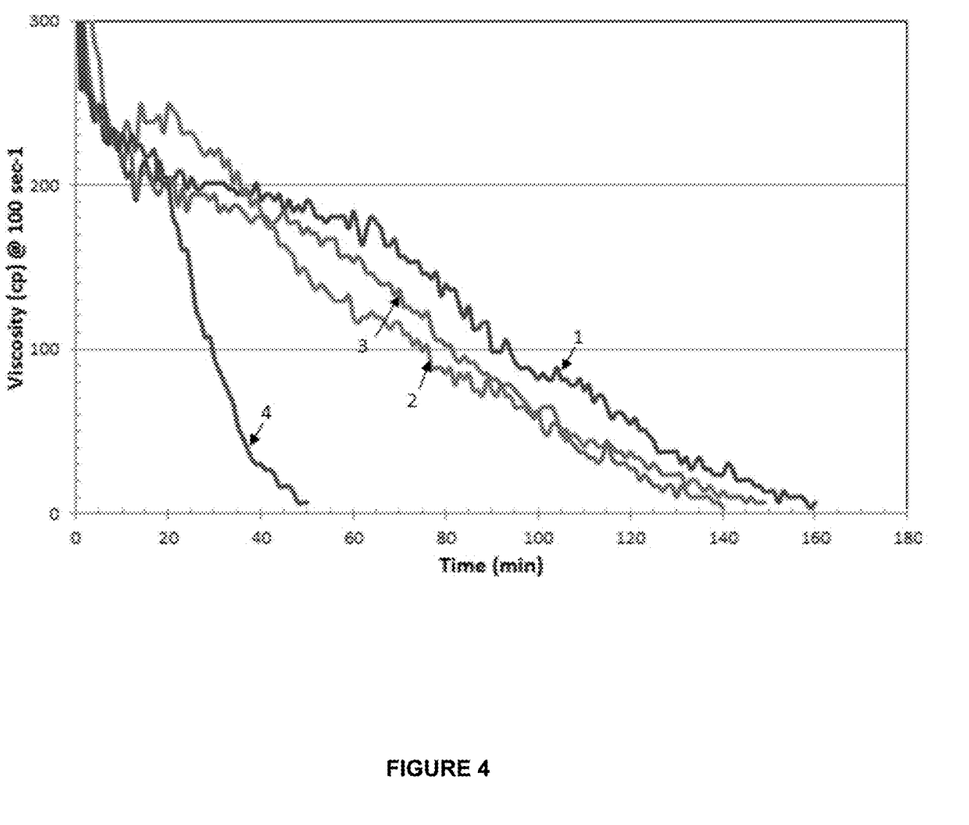
FIG. 4 is a chart of the gel break data for crosslinked fluids prepared according to the method disclosed herein.

The testing for FIG. 4 is set out below:

TABLE C4

Data for FIG. 4 Stability Chart

| Additives | Units | TEST1 Amount | TEST2 Amount | TEST3 Amount | TEST4 Amount |
|---|---|---|---|---|---|
| 47% Guar Slurry | l/m3 | 4.50 | 4.50 | 4.50 | 4.50 |
| 10.2% Formic Acid | l/m3 | 5.30 | 5.30 | — | — |
| 23.3% Formic Acid | l/m3 | — | — | 2.30 | 2.30 |
| High Temperature EAPB | kg/m3 | 0.20 | 0.30 | 0.40 | — |
| Low Temperature EAPB | kg/m3 | — | — | — | 0.30 |
| 14% KOH | l/m3 | 12.00 | 12.00 | 12.00 | 12.00 |
| 12% Boric Acid Crosslinker | l/m3 | 0.80 | 0.80 | 0.80 | 0.80 |
| Fluid Properties | | | | | |
| Fluid System | | ELE-Stim | ELE-Stim | ELE-Stim | ELE-Stim |
| Source Water | | BakkenPW | BakkenPW | BakkenPW | BakkenPW |
| Test Name | | 150820-1P1 | 150820-3P1 | 150821-1P1 | 150821-2P2 |
| Test Date | M/D/Y | Aug. 20, 2015 | Aug. 20, 2015 | Aug. 21, 2015 | Aug. 21, 2015 |
| Initial pH | | 6.74 | 6.74 | 6.81 | 6.81 |
| Linear pH | pH | 3.94 | 3.94 | 3.93 | 3.93 |
| Linear Viscosity | cP | 14.00 | 14.00 | 15.00 | 15.00 |
| Crosslinked pH | pH | 8.80 | 8.63 | 8.86 | 8.84 |
| Test Temperature | ° C. | 70.1 | 70.0 | 70.0 | 70.0 |
| Break Profile | | | | | |
| Initial Viscosity | cP | 355 | 593 | 440 | 425 |
| 15 min Viscosity | cP | 215 | 239 | 208 | 218 |
| 30 min Viscosity | cP | 201 | 218 | 194 | 84 |
| 60 min Viscosity | cP | 184 | 119 | 153 | — |
| Break Time (10 cP) | hh:mm:ss | 2:38:05 | 2:27:05 | 2:18:05 | 0:48:05 |

The Bakken produced water is significantly 'hard' with high levels of divalent cations. It was surprisingly found that we did not require any water treating or softening in order to achieve a satisfactory crosslink.

Reduced Boron Addition

We also found that reducing the amount of boron-based crosslinker was also beneficial. In the attached "Crosslinking of Guar in Bakken Produced Water for Frac", we used 0.8 L/m3 of a 12% Neutralized Boric Acid crosslinker with a Guar slurry loading at 4.5 L/m3. Normally we would use 1.5-2 L/m3 of the crosslinker.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method of forming a cross linked fracturing fluid using produced water, comprising:
   i) mixing a produced brine water having a TDS content of at least 45,000 mg/L with a crosslinkable polymer;
   ii) adjusting the pH of the water for hydration, if necessary, by adding acid prior to or with the addition of the polymer to the produced water;
   iii) allowing the polymer to hydrate in the water;
   iv) adding a crosslinker and, if necessary, adding a base with or after the addition of the crosslinker, wherein the base is added to adjust the pH of the water for crosslinking, to form a crosslinked fracturing fluid,
   wherein the produced brine water has a boron content of at least 20 mg/L; at least 100 mg/L, or at least 150 mg/L.

2. The method of claim 1 wherein the produced water has a TDS content of at least 50,000; of at least 75,000; of at least 100,000; or of at least 150,000 mg/L.

3. The method of claim 1 wherein the produced water is Bakken produced water.

4. The method of claim 3 wherein the method excludes a water softening step.

5. The method of claim 1 wherein the crosslinker is a borate crosslinker.

6. The method of claim 1, wherein the crosslinkable polymer is guar or a derivative thereof.

7. The method of claim 1 wherein the pH of the water for hydration is between 3-7.

8. The method of claim 1 wherein the pH of the water for crosslinking is between 9-11.

* * * * *